(12) United States Patent
Luthardt et al.

(10) Patent No.: US 7,162,321 B2
(45) Date of Patent: Jan. 9, 2007

(54) METHOD FOR PRODUCING A HIGH-STRENGTH CERAMIC DENTAL PROSTHESIS

(75) Inventors: Ralph Gunnar Luthardt, Goetheallee 17a, Dresden (DE) 01309; Volker Herold, Jena (DE); Martina Johannes, Hermsdorf (DE); Olaf Sandkuhl, Cospeda (DE)

(73) Assignees: Inocermic Gesellschaft Fuer Innovative Keyamik MBH, Hermsdorf (DE); Ralph Gunnar Luthardt, Dresden (DE)

( * ) Notice: Subject to any disclaimer, the term of this patent is extended or adjusted under 35 U.S.C. 154(b) by 216 days.

(21) Appl. No.: 10/149,054

(22) PCT Filed: Dec. 7, 2000

(86) PCT No.: PCT/EP00/12599

§ 371 (c)(1),
(2), (4) Date: Nov. 5, 2002

(87) PCT Pub. No.: WO01/41670

PCT Pub. Date: Jun. 14, 2001

(65) Prior Publication Data

US 2003/0096214 A1 May 22, 2003

(30) Foreign Application Priority Data

Dec. 7, 1999 (DE) .................................. 199 58 881

(51) Int. Cl.
G06F 19/00 (2006.01)
A61C 13/00 (2006.01)

(52) U.S. Cl. ........................ 700/118; 264/16; 433/223

(58) Field of Classification Search ............. 433/201.1, 433/202.1, 212.1; 264/19, 20; 249/54; 493/223; 700/118

See application file for complete search history.

(56) References Cited

U.S. PATENT DOCUMENTS

| 4,970,032 | A | * | 11/1990 | Rotsaert ..................... 264/20 |
| 5,080,589 | A | * | 1/1992 | Oden et al. ............... 433/202.1 |
| 5,106,303 | A | * | 4/1992 | Oden et al. .................. 433/223 |
| 5,728,636 | A | * | 3/1998 | Nawa et al. ................. 501/105 |
| 5,775,912 | A | * | 7/1998 | Panzera et al. ............. 433/223 |
| 6,287,121 | B1 | * | 9/2001 | Guiot et al. ................. 433/218 |
| 6,398,554 | B1 | * | 6/2002 | Perot et al. ................. 433/223 |

FOREIGN PATENT DOCUMENTS

| EP | 0267227 | 5/1988 |
| EP | 0580565 | 1/1994 |
| EP | 0593611 | 4/1994 |
| EP | 0614344 | 9/1994 |
| EP | 0645195 | 3/1995 |

(Continued)

OTHER PUBLICATIONS

1998 CAD/CAM/CIM-Systeme in der restaurativen Zahnmedizin Annette Schmidt et al. Quintessenz 49,11, 1111-1122.

*Primary Examiner*—Todd E. Manahan
(74) *Attorney, Agent, or Firm*—Jordan and Hamburg LLP

(57) ABSTRACT

Tooth restorations are produced starting from data preferably obtained by optical or mechanical digitizing of prepared teeth and/or teeth of one jaw or of both jaws, intraorally, or from jaw models or partial models of one jaw or of both jaws, extraorally, a subsequent CAD construction of aforementioned restorations being produced in the way that an outer mold, in opposition to the oral cavity is constructed by the primary shaping of the tooth restoration, consisting throughout of high strength ceramic material, taking into account sinter shrinkage.

9 Claims, 8 Drawing Sheets

FOREIGN PATENT DOCUMENTS

Figure 1:
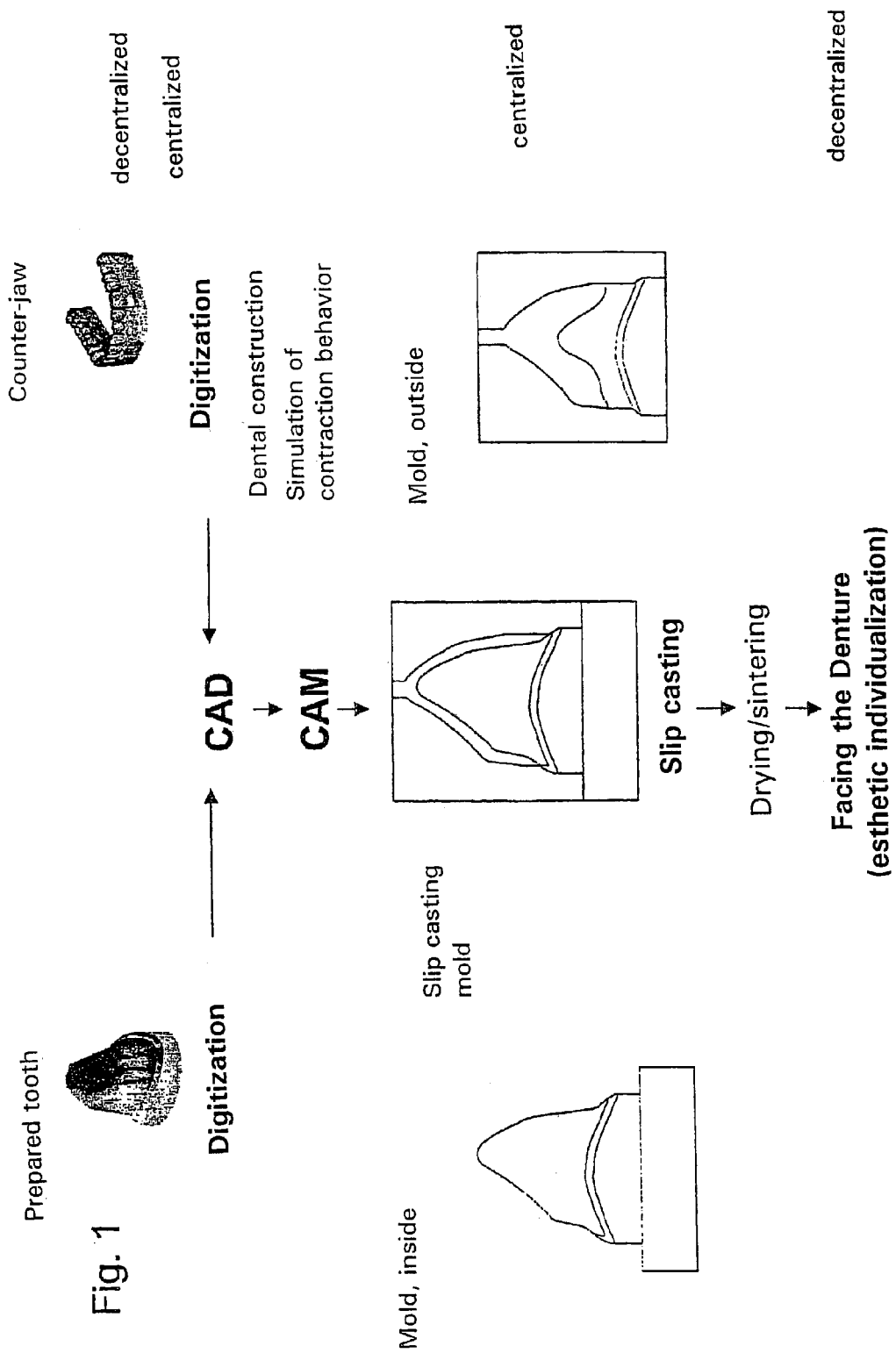

| | | |
|---|---|---|
| EP | 0826642 | 3/1998 |
| EP | 0943296 | 9/1999 |
| JP | 5246760 A1 * | 9/1993 |
| WO | WO 9427517 A1 * | 12/1994 |
| WO | WO 96/29951 | 10/1996 |

* cited by examiner

METHOD FOR PRODUCING A HIGH-STRENGTH CERAMIC DENTAL PROSTHESIS

The invention relates to a method for producing a ceramic tooth restoration such as inlays, onlays, crowns, partial crowns, bridges, implant suprastructures as well as a high strength ceramic tooth restoration made by said method. Ceramic is known in different designs as a material for artificial teeth of all kinds because of its looks and its strength which come nearest to the properties of natural teeth. When the material is appropriately selected, ceramic is at the same time physiologically harmless. Thereby it is rather the required precise final shape which makes up the considerable cost than the material itself, whereby the desired high strength of the tooth restoration and the finishing workability of the same in the fired state of the ceramic are opposing each other.

Furthermore, it is generally known to cast the tooth restorations from special metal alloys, whereby, for example, the inner shape corresponding to a tooth stump will be derived via an impression. This procedure is limited to castable metal alloys.

Furthermore, it is known to copy a pre-manufactured model of the tooth restoration in that a tracer pin is moved along the model, said tracer pin controlling synchronously to its movements a grinding disc and a grinding body, respectively, for working a green body of a tooth restoration (EP 0 267 227 B2). Thereby, in principle, materials of nearly any desired hardness and strength are workable such as, for example, ceramic material. However, this requires a very complicated mechanism and, yet, the working of very delicate details, in particular as concerns indentions and undercuts, is limited due to the finite dimensions of the grinding disc and the grinding body, respectively.

There are also known CAD/CAM methods for three-dimensional milling of hard fired ceramic solid material for the manufacture of tooth restorations in which information, partly even patient specific ones, such as color, material and occlusion registering are fed into the computer. These information are then on-screen processed. Furthermore, an onscreen selection and "modelling" of "crown models", which are stored in a data base, is carried out (Paper by A. Schmidt, M. Walter, K. Boning "CAD/CAM/CIM-Systeme in der restaurativen Zahnmedizin", Quintessenz 49, 11, S. 1111–1122 (1998)). Although here, compared to the prior art discussed herein above a greater variety of forms and fidelity in detail are possible without the urgent necessity to manufacture models, there remains as a disadvantage the high expenditures in working the hard (fired) ceramic material.

Hard tooth restoration green bodies can be brought into the desired final shape by erosion processes such as ultrasonic erosion or electroerosion, whereby the working tools such as sonotrodes and electroerosion electrodes have been manufactured before from impressions and models, respectively, as accurate complementary images of the desired shape. The electroerosion process is, in principle, limited to electrically conductive material, whereas the ultrasonic erosion does not have this limitation and will be particularly used with ceramic material. By a division along the so-called "equator", it is possible to work both, the cervical side (the side opposing the jaw) and the occlusal side respectively the incisal side (the side opposing the buccal cavity) (EP 0 645 195 A1). A combination of both erosion principles permits according to a well-devised proceeding a true-to-size manufacture of a ceramic tooth restoration or of a metal crown, whereby even a set of roughing tools and refined abrading tools can be manufactured on models manufactured before by galvanic deposition, and prior departures in fitting precision are purported to be overcome (EP 0 614 34.4 B 1). The operational sequence will be differentiated whether ceramics or metal is to be worked, whereby the use of the spark erosion requires forming tools made of graphite in this case. As disadvantages of these methods remain the long processing time and, above all, as to the proceedings according to the second mentioned publication, the great number of different succeeding steps of the proceeding which have to be synchronized to one another.

As to the manufacture of the so-called jacket crowns, it is known to isostatically press a pre-manufactured flexible ceramic foil in its plastic raw state upon a plaster model of the inner form. Said plaster model has been computer aided modeled before in analogy to the tooth stump with an added measure for consideration of the sintering shrinkage of the ceramic material (EP 0 826 642 A1). Since the foil is produced with a definite thickness which in the course of its transformation on the model can only slightly be shaped without tearing, this method is limited to the manufacture of crowns and cannot be applied to other types of tooth restorations.

Finally, it is known to manufacture the cervical shape of a tooth restoration on a model, for example in plaster, by dry pressing or also by slip casting, whereby the tooth restoration is fitted on at least one prepared surface of a tooth stump or artificial abutments. The occlusal form of the tooth restoration is veneered with dental porcelain fired to the surface. The model has been manufactured before by means of a computer controlled milling machine in dependence on a three-dimensional scanning directly in the mouth or on a casting model, considering the later sintering shrinkage and a gap for the cement for fixing (EP 0 580 565 BI, corresponds to DE 693 20 563 T2, WO 94/27 517 A1). With respect to the occlusal form of the tooth restoration there has only been said that the outer surface of the core of the tooth restoration produced in this way should have a form "near the desired size", hence, the masticatory surfaces cannot be directly manufacture by said method, but require an aftertreatment in the fired state. This, however, necessitates further method steps with at least the same demands for fitting precision as well as for appearance and fidelity of detail which, in total, at least doubles the expenditures for working. The dry pressing of parts made of high-duty ceramics has the disadvantage of non-uniform densification in the course of shaping, which leads to defects in the form of a partially porous structure remaining after firing and sintering, respectively.

A further known and very complicated and material expensive method for manufacturing ceramic tooth restorations purports to avoid the final shaping procedure in the ready-sintered (hard) state, which procedure has been referred to hereinabove and which is particularly critical owing to the tool wear. It further purports to solve at the same time the problem of the thin edge portions of a tooth restoration which as a result of the sintering shrinkage distort or become brittle. To this end, the negative outer shape and inner shape of a tooth restoration will be worked out from a cold densifed or partly sintered green body form under consideration of the sintering shrinkage. The tooth restoration is shaped out of the chips resulting from the working or from a similar material in this mold and ready sintered, whereby said mold is additionally treated with a mold release agent (WO 96/29951 A2). Thereby one can do without the manufacture of a wax model or a plastic mold, in that, for use in the computer-aided manufacture of the mold, the inlay outer shape as well as the cavity shape and the shape of the prepared tooth stump, respectively, are in-line detected by a sensing within the mouth of the patient. The disadvantages of this technical solution lie in the long time required for the manufacturing procedure as well as in the expenditures therefor rather than in the quality of the tooth restorations manufactured in this way.

Tooth restorations made of aluminum oxide, with additives, if necessary, as well as made of zirconium oxide are known, independent of a certain manufacturing method for the same (EP 0 593 611 B1).

Starting from the above described prior art, the object of the present invention is to provide a method for producing a tooth restoration, in particular a tight-fitting ceramic tooth restoration, in which under avoidance of a hard-worked ceramic material and with a minimum of method steps, the outer shape of the ceramic tooth restoration being in opposition to the oral cavity including the gradually thinning down restoration edge is manufactured in its final shape, whereby the sintering shrinkage is being taken into consideration.

Starting from data which have preferably been derived from intraoral or extraoral optical and/or mechanical digitizing of tooth stumps and/or dental technological restorations such as inlays, onlays, crowns, partial crowns, bridges, implant suprastructures, respectively from the structures of all restorations mentioned herein before and/or ready-to-use dentures and/or teeth of one jaw or of both jaws and/or models or partial models of one jaw or of both jaws, and/or by CAD constructions of inlays, onlays, crowns, partial crowns, bridges, implant suprastructures as well as the structures of all restorations mentioned herein before, the object is realized according to the present invention in that for the primary shaping of the tooth restoration a mold, corresponding at least to the outer shape of the tooth restoration, is manufactured which is enlarged and reduced, respectively, by the three-dimensional variation of dimension occurring in the course of the primary shaping. Depending on the form of the tooth restoration to be manufactured, one-part or multipartite molds will be employed. One-part molds will preferably be used when the tooth restoration to be manufactured is of a geometry free of undercut. When the tooth restorations to be manufactured are of more complex geometries preferably bipartite or, if necessary, multipartite molds will be used. Undercut shapes will naturally result from the manufacture of partial crowns, crowns or with tooth restorations for reconstruction of the functional masticatory surfaces and/or bridges and/or implant superstructures. Thereby the separating planes preferably lie in the range of the anatomic equator of the tooth restoration.

The term "primary shaping" (in German, "Urformung", as used throughout the specification is to be understood as the manufacturing of a solid body out of unshaped material by providing cohesion thereto, as defined in Dubbels, "Taschenbuch fuer den Maschinenbau", 19$^{th}$ edition, Berlin 1997, page 4, by reference to German standard DIN 8580.

The geometry of the mold defines the outer shape of a ceramic tooth restoration when a one-part mold is concerned, whereas the shaping of the inner shape of the tooth restoration can be achieved, abrasingly, by eroding or by cutting, for example, by grinding or milling of the green body, the brown body or in the sintered state. The working will be preferably based on CAD-working data comprising the data base of the inner shape and of the outer shape. Alternatively, the working is also possible by conventional technologies such as copy grinding and copy milling, respectively. The three-dimensional association of the shapes in the working machines is preferably carried out via reference planes and clamping reference surfaces. Alternatively, a positioning by the workpiece is possible.

In the case of a multipartite form, the geometry of the mold defines the outer shape and in most cases also the inner shape of the tooth restoration. Thereby the outer shape of the tooth restoration will be worked as a negative, whereas the inner shape of the tooth restoration will be worked as a positive. In the case of crowns or partial crowns or inlays, the cervical parts of the restoration are defined preferably together with the inner shape. In the case of FPDs, there also will be defined, preferably together with the inner shape of the bridge, the basal surface of the pontic. The three-dimensional association of the partial shapes to each other is preferably carried out via reference planes and clamping reference surfaces.

By the construction of the shape of the tooth restoration, which preferably is accomplished by CAD/CAM technologies, it is possible to computer aided simulate and to compute the three-dimensional dimension variations occurring in the course of primary shaping (Urformung) for each restoration. The digitized data of the prepared teeth serve as a basis for the dental CAD/CAM technologies obtained by intra-oral or extra-oral, optical or mechanical measuring of the teeth, of models or partial models of one jaw or of both jaws with or without the detection of the: spatial association of the upper jaw and the lower jaw. Optionally the digitizing data of the neighboring teeth are utilized for the design of the approximal portions of the inlays, onlays, crowns, partial crowns, bridges, and implant suprastructures and of the structures, respectively, of all restorations mentioned above as well as the digitized data of the antagonistic teeth in the reconstruction of the functional masticatory surfaces of the restorations to be manufactured. It is possible to optimize the quality of the reconstruction of the masticatory surfaces of the inlays, onlays, crowns, partial crowns, bridges, and implant suprastructures and of the structures, respectively, of all restorations mentioned above by utilizing the digital data of the upper jaw and the lower jaw in combination with the data of the movement pattern of the mandibular joints.

Into the simulation of the three-dimensional dimension variations of the material in the course of the primary shaping, there are integrated the data of the prepared teeth, the geometry of the constructed inlays, onlays, crowns, partial crowns, bridges, and implant suprastructures and of the structures, respectively, of all restorations mentioned above, furthermore the layer thickness of the dental fixing material as well as the technological parameter of the mold material, of the ceramic material, and of further procedural performance influencing factors of the respective primary shaping process. Thereby one-part molds are preferably made from block material. In the case of more complex geometries or under-cut outer shapes of the tooth restorations to be manufactured, a separation of the mold into at least two parts is necessary. To this end, special pre-manufactured blanks for partial molds which preferably consider the separation planes and the inlet gates or injection ports for the respective shaping method are used. The individual partial molds are bi-uniquely associated to each other via reference planes and clamping reference surfaces. Thereby the machining of the partial molds is performed by three-axial or multi-axial machinery.

The material-used for the manufacture of tooth restorations preferably are ceramics, in particular high strength and high-purity ceramics ($Al_2O_3$, partly stabilized or fully-stabilized $ZrO_2$), dispersed ceramics) of mean grain size within the grain structure <1 μm, but also metals. For improving the esthetic appearance of the tooth restoration, both, high strength transparent ceramic material and such ones being colored in accordance with the 16 so-called "vita-colors" are utilized. It is also possible to use gradient material for optimizing the optical and/or mechanical properties. A possible esthetic optimizing of the restorations to be manufactured preferably is achieved by means of dopants in the ppm-range.

The primary shaping of the inlays, onlays, crowns, bridges, and implant suprastructures and of the structures, respectively, of all restorations mentioned above is preferably carried out by ceramic slip casting or ceramic injection molding.

By virtue of the present invention it is possible to have a principally more favorably priced shaping of the tooth restoration, in that the shaping by cutting is shifted from the hard-machining of the ceramic to the considerably softer material of the mold for the primary shaping, such as plaster. Thereby one has to consider that the tooth restoration aiming at the reconstruction of the occlusal (masticatory) surfaces is characterized in particular by the composite and complex shape of the outer shape, whereas the already commonly used computer aided manufacture of the inner shape is comparatively simple.

The tooth restoration is realized by maintaining the strength inherent in the respective material ("as fired").

By virtue of the use of the present invention, the manufacture of the metal-free tooth restoration such as, for example, inlays, onlays, partial crowns, crowns, bridges, and implant suprastructures as well as bridges with functional, masticatory surfaces becomes possible which satisfy without any reworking the esthetic and biological requirements to a definitive prosthetic treatment.

Figure 2:
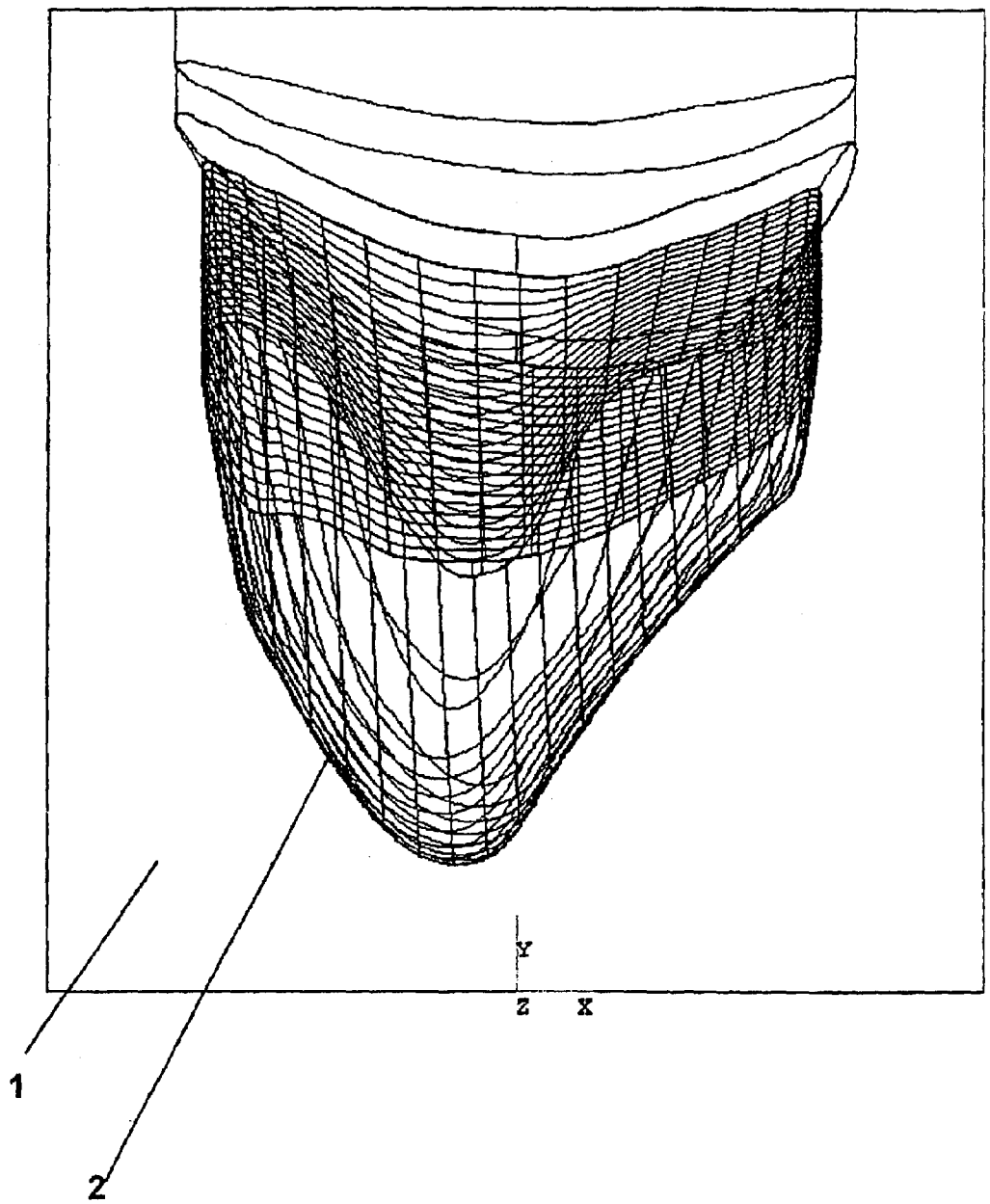
Figure 3:
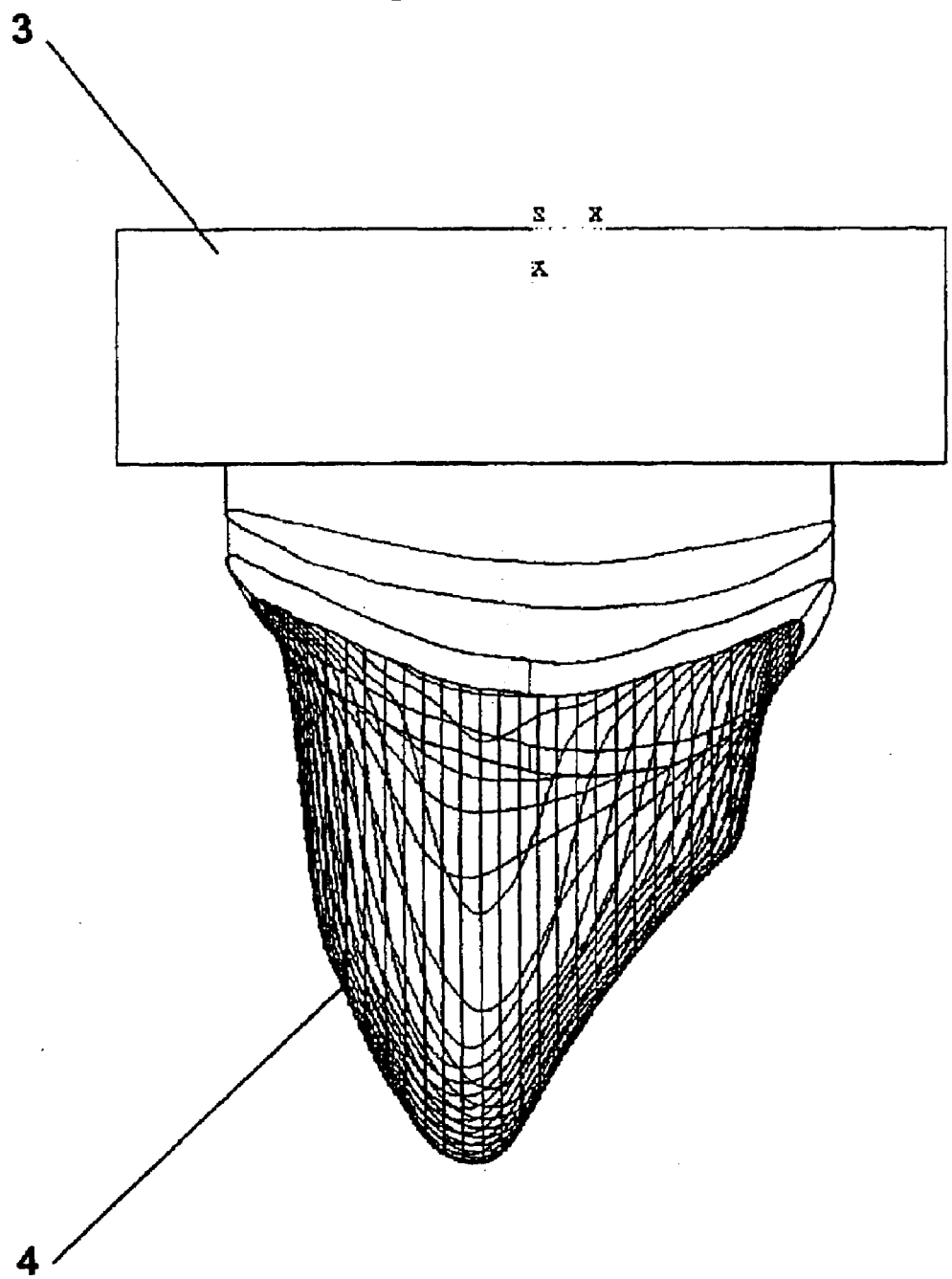
Figure 4:
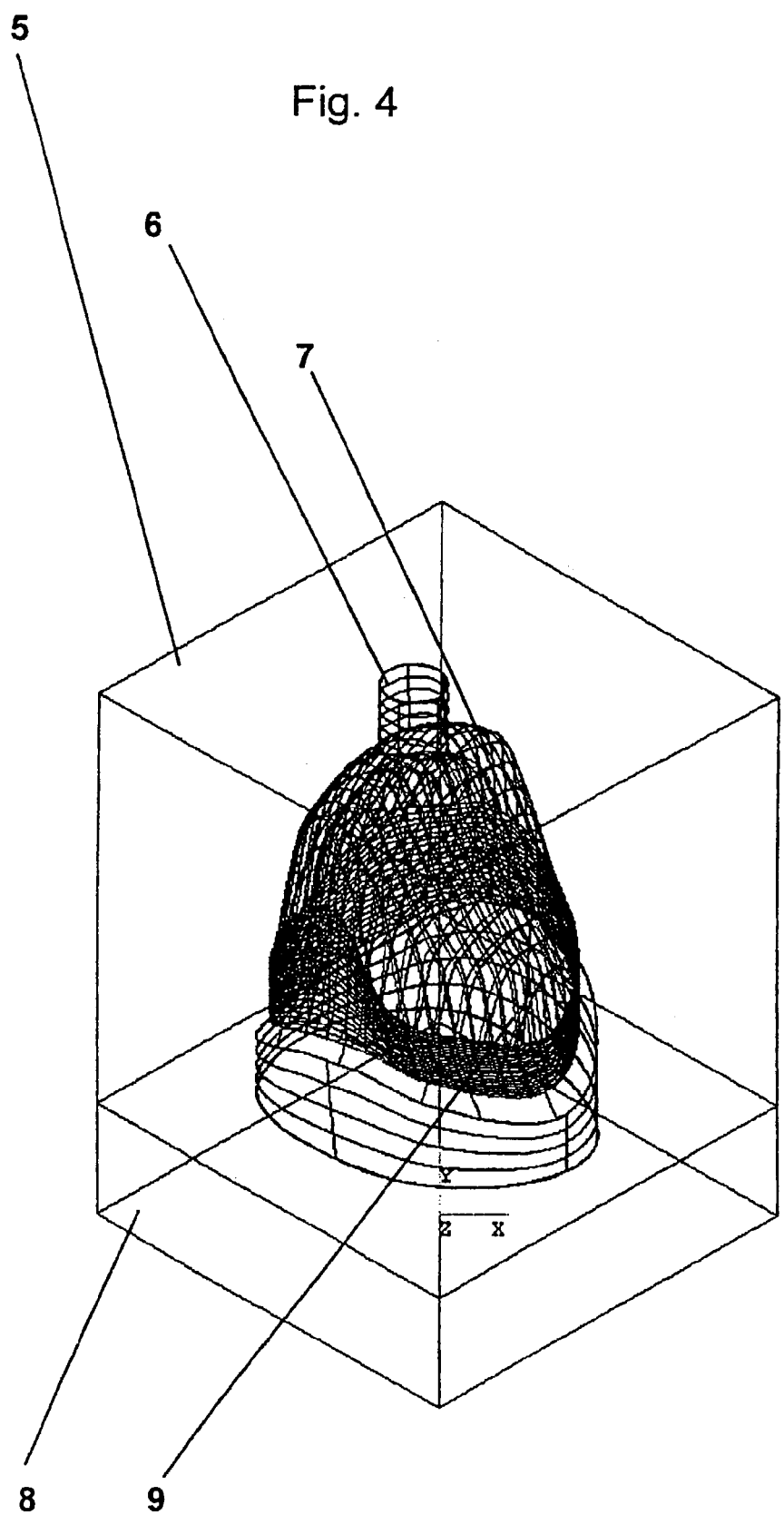
Figure 5:
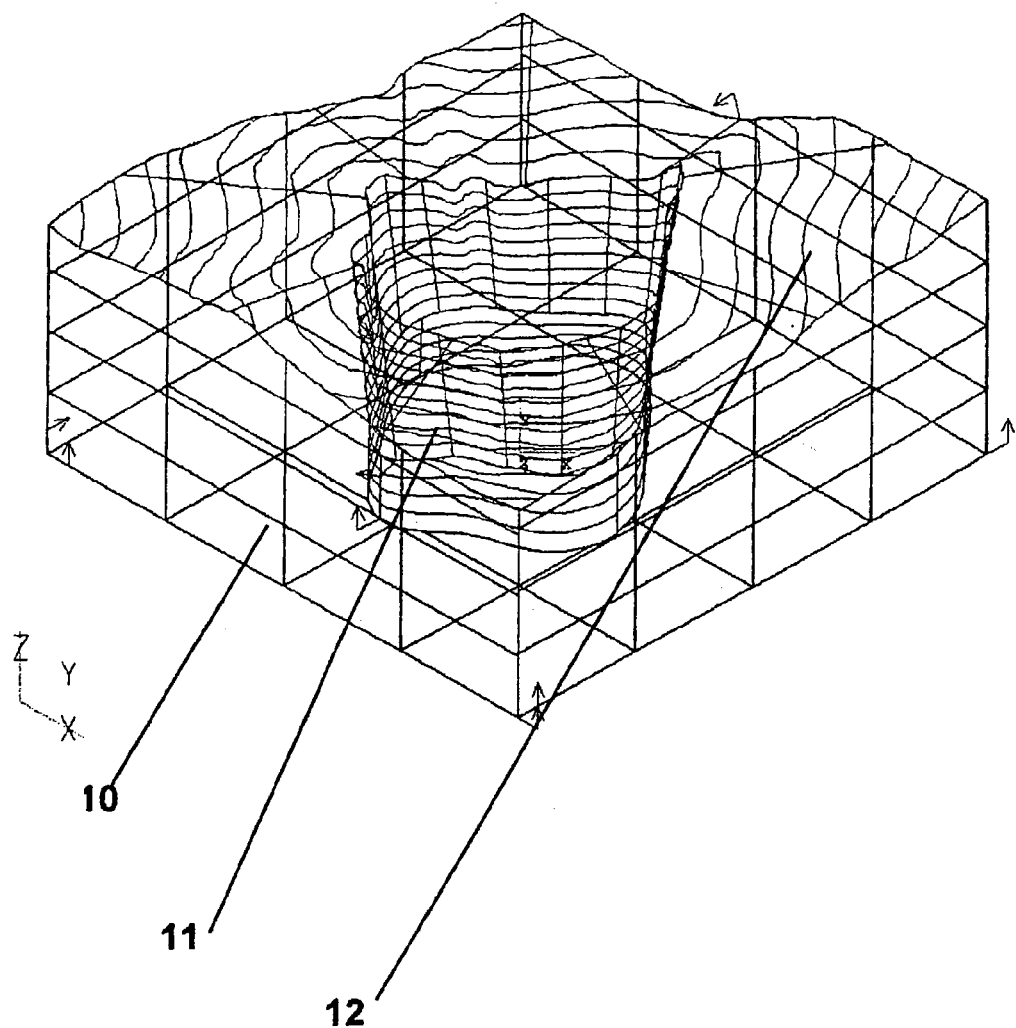
Figure 6:
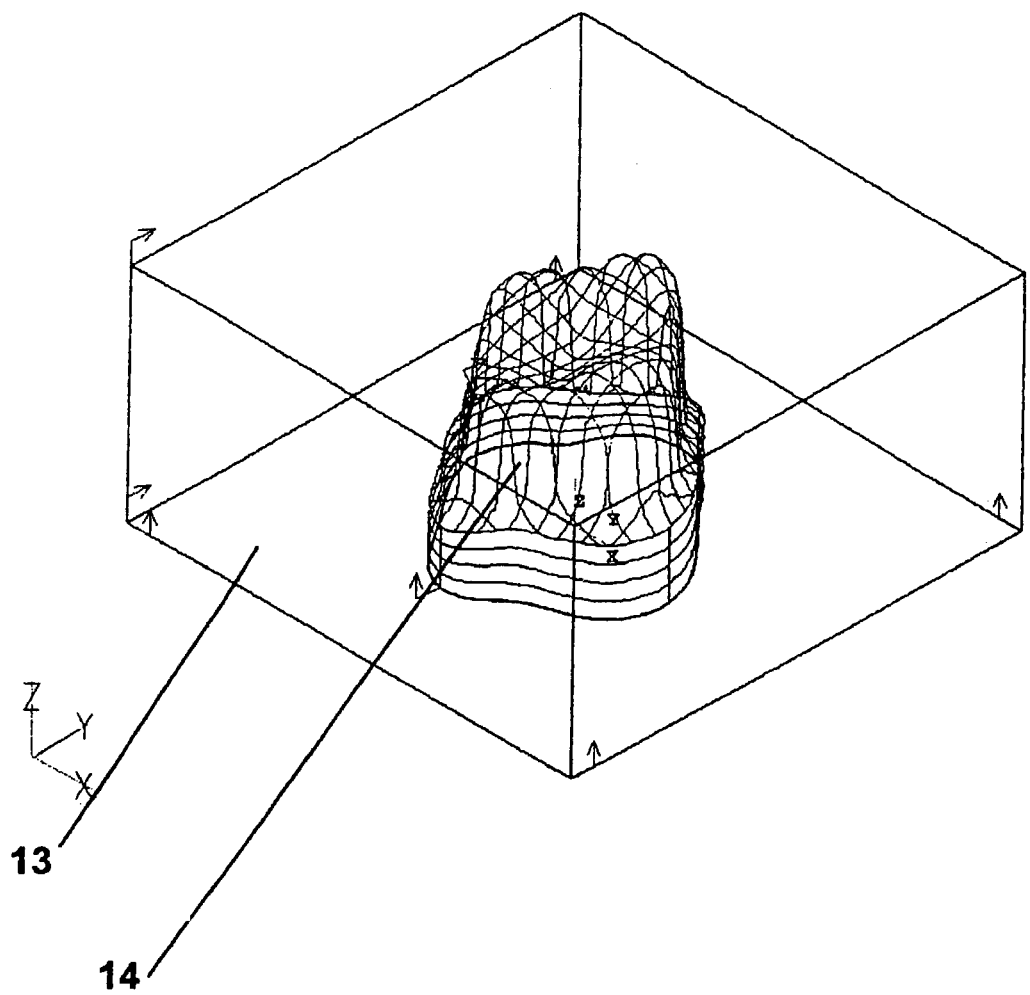
Figure 7:
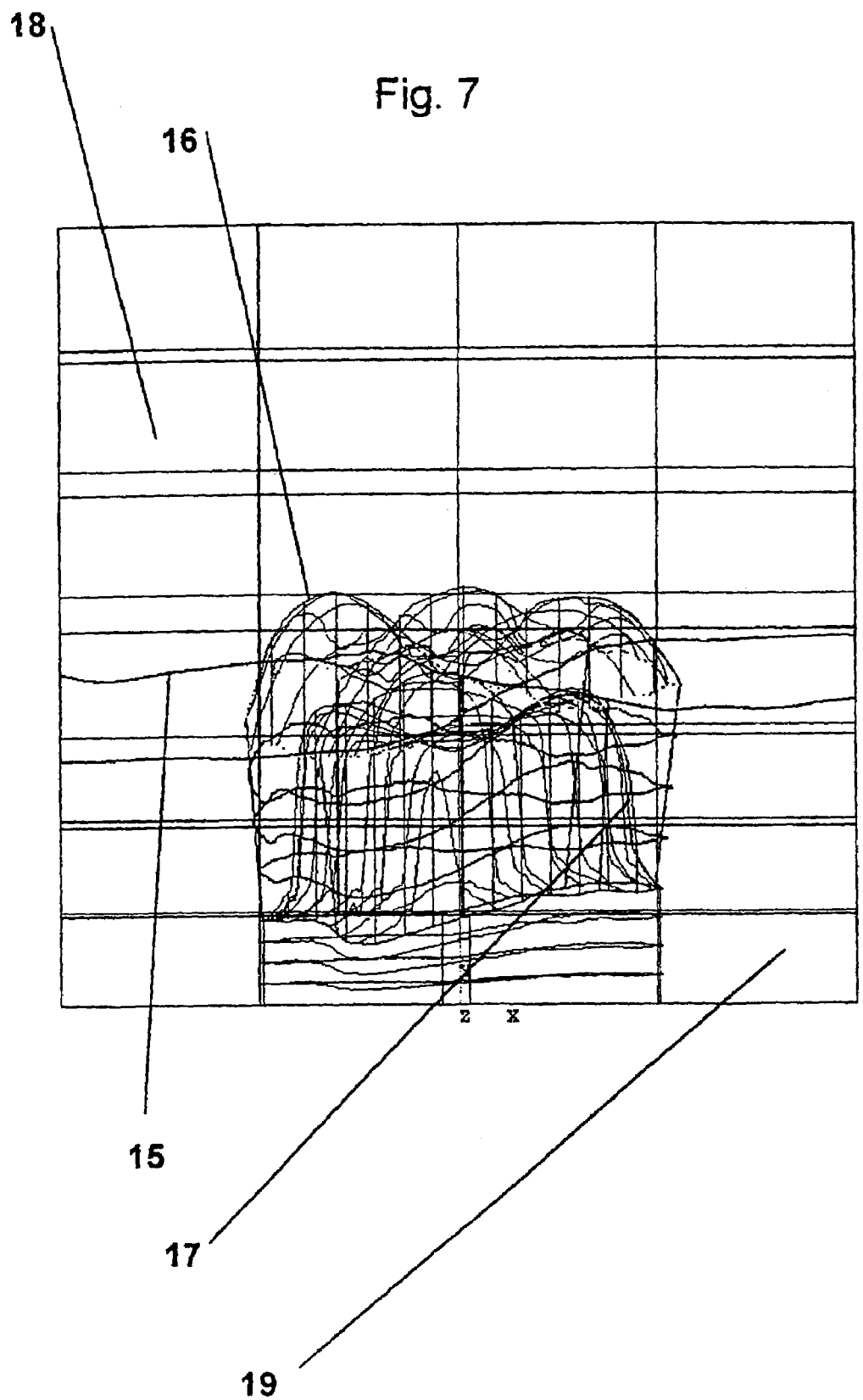
Figure 8:
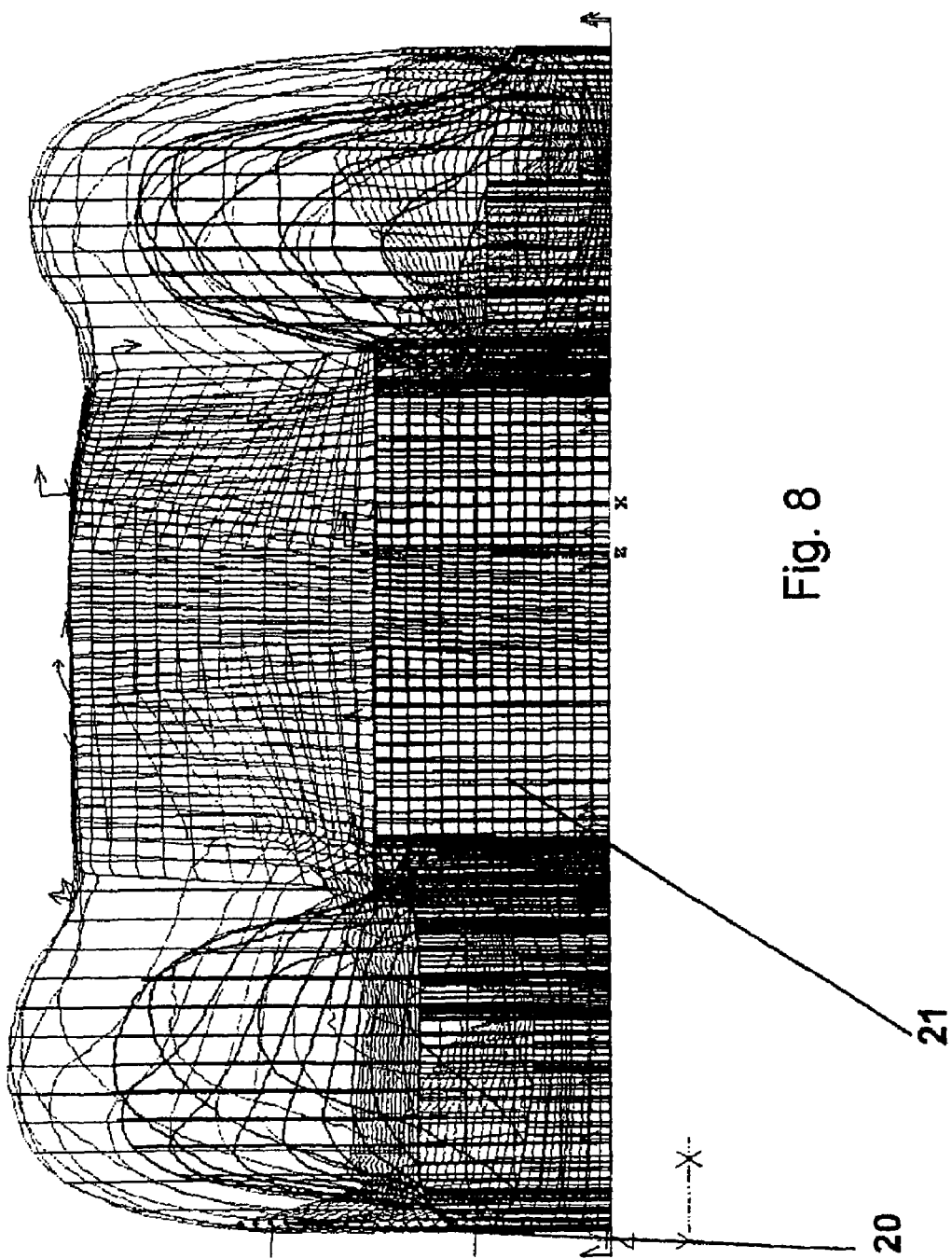

Further details and features of the method according to the present invention will become apparent from the following description of the embodiments in connection with the drawings. There is shown in:

FIG. 1 a representation of the principle proceeding in manufacturing a tooth restoration according to the inventional method, FIG. 2 a representation of a one-part casting mold according to the inventional method with an outer shape of a crown structure, FIG. 3 a representation of a casting mold according to the inventional method with an inner shape of a crown structure, FIG. 4 a perspective representation of a bi-partite casting mold according to the inventional method, FIG. 5 a perspective representation of a casting mold according to the inventional method with an outer shape of a crown including a functional masticatory surface, FIG. 6 a representation of a casting mold according to the inventional method with an inner shape of a crown, FIG. 7 a representation of a bi-partite casting mold of a crown with a functional masticatory surface according to the inventional method, FIG. 8 a representation of a bi-partite casting mold of a bridge structure.

The sequence of the inventional method steps (FIG. 1) permits an optimizing with respect to the costs by a splitting up of the method step into such being centralized and such which have to be carried out decentralized. CAD/CAM service provider and specialized dental technicians, respectively, who operate for a plurality of clients, cooperate, for example, in the following suitable, but of course not compulsory, splitting up of the operations:

Inventional decentralized dental treatment with preparation;

Shaping and manufacture of precision models and the optical digitizing of the same and a direct intra-oral digitizing, respectively;

Central computation of the geometric shape of the mold for the slipcasting under consideration of the simulated shrinkage behavior;

Central generation of the CNC-program for working the individual molds for the slipcasting as well as the manufacture of the same;

Central casting and sintering of the tooth restoration;

If necessary, decentralized esthetic individualizing of the tooth restoration.

The forms in FIG. 2 to 7, illustrate the system of reference planes and clamping reference surfaces by the respective X-, Y-, and Z-axes. These forms serve to realize the method for manufacturing ceramic tooth restorations as well as high strength ceramic tooth restorations manufactured by said method. These forms are composed of the one-part mold or the multipartite mold (FIG. 3) which is comprised of the outer mold half 1 and the outer mold half 5, 10, 18, respectively, and the inner mold half 3, 8, 13, 19 for defining the outer shape 2 and the outer shape 7, 11, 16, and 20, respectively, and the inner shape 9, 14, 17, 21 of the restoration to be manufactured, furthermore, of the system of casting channels 6 as well as the separation planes 12 and 15, respectively. Fig. 2 shows an outer shape free from undercut which, in principle, permits a one-part mold for defining the outer shape 1 of the restoration to be manufactured. Together with the inner mold half 3 shown in FIG. 3 defining the inner shape 4 of the restoration, these can be assembled to a multipartite mold (FIG. 4). Furthermore, FIG. 4 shows the casting channel 6 as well as the separation plane. More complex separation surfaces 12 and 15, respectively, result from an increasing complexity of the geometry of the restorations to be manufactured (FIG. 5, 6, 7). FIG. 8 shows the outer shape and the (20 and 21, respectively) of a bridge.

The invention will be further explained as concerns the material by virtue of two embodiments.

EXAMPLE OF EMBODIMENT 1

A drum mill is charged with 500 g aluminum oxide of a grain size of $d_{50}=0.2$ μm together with 0.05 weight % magnesium carbonate, and 1.5 weight % of a known liquefier for preparing a casting slip as well as water. The weight ratio of material to be milled:milling bodies is 1:6. After a milling time of 24 hours the slip is removed. Its solids content is 71.0 weight %. For manufacturing a crown, this slip is filled into the casting mold which has been modeled according to the scheme of the illustration. After a solidification time of about 30 minutes the crown is demolded and, after appropriate drying it will be fired at a hold-up time for 2 hours at 1350° C.

EXAMPLE OF EMBODIMENT 2

A batch of 500 g of 80 weight % aluminum oxide and 20 weight % partly stabilized zirconium oxide of a grain size of $d_{50}=0.3$ μm are processed in analogy to embodiment 1. The only difference is that sintering is carried out at 1400° C.

LIST OF REFERENCE NUMERALS

1 outer mold half
2 outer shape
3 inner mold half 4 inner shape
5 outer mold half
6 casting channel
7 outer shape
8 inner mold half
9 inner shape
10 outer mold half
11 outer shape
12 separation plane
13 inner mold half
14 inner shape
15 separation plane
16 outer shape
17 inner shape
18 outer mold half
19 inner mold half
20 outer shape
21 inner shape

The invention claimed is:

1. Method for producing high strength ceramic dental restorations including inlays, onlays, partial crowns, crowns, FPDs and superstructures for implant retained prosthesis, that can be fitted onto at least one prepared surface of a tooth stump or artificial abutment, said restoration having an internal geometry determined by a border surface occurring between said prepared surface and said restoration, and an external geometry, said method comprising making data available to define said internal geometry by means of digitization of the prepared surface and using said data to form the inner shape of said restoration and using digitization to obtain data defining a negative form of neighboring and antagonistic teeth and masticatory faces of said restoration as said external geometry, and using said latter data to construct a mold, and utilizing said mold to form the outer shape of said restoration, said method steps resulting in the forming of said dental restoration consisting throughout of said high strength ceramic for its final shape.

2. Method as claimed in claim 1, further comprising producing a reproduction of physiological natural masticatory faces having respective depth of fissures and fissure radii by slip casting in a primary shaping procedure.

3. Method as claimed in claim 1 or 2, wherein the outer shape of the restoration is reduced by an amount corresponding to a subsequent ceramic veneering.

4. Method as claimed in claim 1 or 2, wherein the high strength ceramic material is differently colored by means of dopants to simulate coloring of a natural tooth.

5. Method as claimed in claim 1 or 2, wherein the high strength ceramic material is transparent.

6. Method as claimed in claim 1 or 2, wherein in the course of primary shaping the ceramic dental restoration is given, taking into consideration the layer thickness of dental bonding material, a final inner shape in opposition to the jaw and to the prepared surface, respectively, said final inner shape being obtained by an impression.

7. Method as claimed in claim 1 or 2, wherein shaping of the inner shape is carried out by machining the ceramic as a green body, a brown body or in the sintered state.

8. Method as claimed in claim 1, wherein the primary shaping is carried out by ceramic injection molding.

9. Method as claimed in claim 1 including the step of using said data to form the inner shape of said restoration in the construction of said mold and subsequently utilizing the mold for the primary shaping of the restoration including both its inner and outer shapes.

* * * * *